United States Patent [19]

Shepherd

[11] 4,382,143

[45] May 3, 1983

[54] HYPOLIPIDEMIC AND ANTIATHEROSCLEROTIC NOVEL (MONOSUBSTITUTED-AMINO)HETEROARYL CARBOXYLIC ACIDS AND ANALOGS

[75] Inventor: Robert G. Shepherd, South Nyack, N.Y.

[73] Assignee: American Cyanamid Company, Stamford, Conn.

[21] Appl. No.: 60,251

[22] Filed: Jul. 23, 1979

[51] Int. Cl.³ .................. C07D 333/40; C07D 333/38
[52] U.S. Cl. .................................. 549/68; 549/61; 549/69; 424/251; 424/263; 424/267; 424/270; 424/272; 424/273 P; 424/274; 424/275; 424/285; 542/400; 544/332; 546/193; 546/194; 546/207; 546/208; 546/209; 546/211; 546/212; 546/261; 546/264; 546/279; 546/280; 546/281; 546/283; 546/284; 546/310; 548/336; 548/518; 548/527; 548/532
[58] Field of Search .......................................... 549/68

[56] References Cited

U.S. PATENT DOCUMENTS

| | | | |
|---|---|---|---|
| 3,787,478 | 1/1974 | Dolejs et al. | 260/471 R |
| 3,803,211 | 4/1974 | Dolejs et al. | 260/471 R |
| 3,823,161 | 7/1974 | Lesser | 549/68 |
| 4,230,872 | 10/1980 | Klaus et al. | 549/68 |

FOREIGN PATENT DOCUMENTS

| | | |
|---|---|---|
| 2128314 | 1/1972 | Fed. Rep. of Germany . |
| 2338819 | 2/1974 | Fed. Rep. of Germany . |
| 2246237 | 5/1975 | France . |
| 2340726 | 9/1977 | France . |

OTHER PUBLICATIONS

Allais et al.; Chem. Abs. vol. 82:31272n (1975) (abstract of Fr. Demande 2,198,736).

*Primary Examiner*—Mary C. Lee
*Attorney, Agent, or Firm*—Robert P. Raymond

[57] ABSTRACT

This disclosure described novel (monosubstituted-amino)heteroaryl carboxylic acids and analogs which are useful as hypolipidemic and antiatherosclerotic agents.

1 Claim, No Drawings

HYPOLIPIDEMIC AND ANTIATHEROSCLEROTIC NOVEL (MONOSUBSTITUTED-AMINO)HETEROARYL CARBOXYLIC ACIDS AND ANALOGS

BRIEF SUMMARY OF THE INVENTION

This invention relates to new organic compounds and, more particularly, is concerned with (monosubstituted-amino)heteroaryl carboxylic acids and analogs which may be represented by the formula

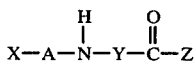

$$X-A-\underset{\underset{H}{|}}{N}-Y-\underset{\underset{O}{\|}}{C}-Z \qquad I$$

wherein X is selected from the group consisting of hydrogen, $C_3$–$C_8$ cycloalkyl, and substituted or unsubstituted aryl; A is a divalent radical selected from the group consisting of branched or unbranched $C_6$–$C_{19}$ alkylene, alkenylene, and alkynylene; Y is a 5- or 6-membered heteroaryl ring containing one or more nitrogen, sulfur, or oxygen atoms and optionally unsubstituted or substituted with one fluoro; and Z is selected from the group consisting of hydrogen, hydroxy, loweralkoxy, loweralkoxyloweralkoxy, diloweralkylaminoloweralkoxy, (mono- or polyhydroxy)loweralkoxy, (mono- or polycarboxy)loweralkoxy, (mono- or polycarboxy)hydroxyloweralkoxy, allyloxy, 2,3-epoxypropoxy, substituted or unsubstituted-(phenoxy, benzyloxy, or 3-pyridyloxy), pyridylmethoxy, tetrahydropyranyloxy, (mono- or polyhydroxy)alkylamino, allylamino, propargylamino, 2-sulfoethylamino, (mono- or polycarboxyl)loweralkylamino, loweralkanoylamino, (substituted or unsubstituted)aroylamino, loweralkanesulfonylamino, (substituted or unsubstituted)arenesulfonylamino, loweralkanylhydrazino, hydroxylamino, polymethyleneimino, and (4-carboxy- or 4-carboethoxy)thiazolidino; and the pharmaceutically acceptable non-toxic acid-addition and cationic salts thereof.

The loweralkyl, loweralkoxy, loweralkanoyl, and loweralkanesulfonyl groups referred to above contain 1 to 6 carbon atoms and are optionally unbranched or branched. The polyhydroxy and polycarboxy groups referred to above contain 2 to 4 hydroxy or carboxy groups, respectively.

Suitable groups contemplated by the present invention for the substituent X are cyclopropyl, cyclopentyl, cyclohexyl, phenyl, 4-chlorophenyl, 4-fluorophenyl, 3-methoxyphenyl, 4-methylphenyl, naphthyl, and the like.

Suitable alkylene, alkenylene and alkynylene groups contemplated by the present invention for the moiety A are, for example, octamethylene, undecamethylene, tetradecamethylene, hexadecamethylene, 3-methylheptamethylene, 1,1,6-trimethylheptamethylene, 1-(n-butyl)pentamethylene, 1-ethyl-1-methylpentamethylene, 2,7-dimethyloctamethylene, 1-(n-octyl)decamethylene, 2-undecenylene, 1-(2-butenyl)decamethylene, 1-(1-methyl-2-propenyl)decamethylene, 1-(n-hexyl)-3-decenylene, 7-hexadecenylene, 9-hexadecenylene, 1-(n-butyl)-3-dodecenylene, 12-hexadecenylene, 3,7,7-trimethyl-2-heptenylene, 1-(n-propyl)-2-heptenylene, 2-decenylene, 9-methyl-2-nonenylene, 1-(n-pentyl)-2-undecenylene, 1-ethyl-2-tridecynylene, 1-(n-hexyl)-4-decynylene, 4-hexadecynylene, and the like.

Suitable heteroaryl rings contemplated by the present invention for the moiety Y are furan, pyrazole, pyridine, pyrimidine, oxazole, pyrrole, thiazole, thiophene, and the like.

Suitable groups contemplated by the present invention for the substituent Z are, for example, methoxy, isopropoxy, 2-ethoxyethoxy, 2-dimethylaminoethoxy, 1-methyl-4-piperidyloxy, 4-pyridylmethoxy, 2,3-dihydroxypropoxy, 2-hydroxypropoxy, 3-hydroxypropoxy, 4-chlorobenzyloxy, 3-methylbenzyloxy, 4-fluorophenoxy, 4-sulfophenoxy, 2,6-dichlorophenoxy, 3-carboxyphenoxy, 2,6-dimethyl-3-pyridyloxy, 6-methoxy-3-pyridyloxy, 2-hydroxy-3-pyridyloxy, 5-carboxy-3-pyridyloxy, carboxymethoxy, 1-methoxycarbonylpropoxy, 2-methoxycarbonyl-2-propoxy, 2,3-dihydroxypropylamino, carboxymethylamino, acetylamino, benzoylamino, 4-chlorobenzoylamino, methanesulfonylamino, p-toluenesulfonylamino, 1-piperidyl, and the like.

A preferred embodiment of the present invention relates to those compounds of formula I wherein X, A, and Z are as defined above and Y is selected from the group consisting of thiophene, furan, pyrrole, pyridine and pyrimidine. A more preferred embodiment of the present invention relates to those compounds in which X is hydrogen; A is as defined above; Y is furan, pyrrole, or thiophene; and Z is hydroxy. The most preferred embodiment of the present invention relates to those compounds in which X is hydrogen; A is as defined above; and Y and Z are selected such that formula I represents a 4- or 5(monosubstituted-amino)-2-thiophenecarboxylic acid, a 5-(monosubstituted-amino)-2-furancarboxylic acid or a 4- or 5-(monosubstituted-amino)-1-methyl-2-pyrrolecarboxylic acid.

The invention also pertains to novel compositions of matter useful as antiatherosclerotic agents and to methods of ameliorating atherosclerosis by counteracting hyperlipemia and arterial plaque formation in mammals therewith; the active ingredients of said compositions of matter being the novel (monosubstituted-amino)heteroaryl carboxylic acids and salts of the present invention. These compounds may be utilized either as such or in the form of a pharmaceutically acceptable salt with an organic or inorganic acid or base. The invention also contemplates a method for lowering serum lipids and for ameliorating atherosclerosis in mammals by the administration of said acids and derivatives.

BACKGROUND OF THE INVENTION

Considerable effort has been directed in recent years to obtain substances useful in counteracting the consequences of hyperlipidemia, a condition involving elevated cholesterol, phospholipid and/or triglyceride levels in the blood, and of hyperlipoproteinemia, involving an imbalance of the lipoproteins. The most serious condition associated with hyperlipidemia and hyperlipoproteinemia is atherosclerosis, a form of arteriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscles and brain, thereby producing permanent damage to these organs. Such damage may lead to ischemic heart disease, congestive heart failure, life-threatening arrhythmias, senility, or stroke. Involvement of leg arteries may lead to gangrene and loss of the limb. It has been known for more than 100 years that cholesterol is a major component of atherosclerotic lesions or plaques. Investigators have been trying to determine the role of cholesterol in lesion initiation and development and also, most importantly, whether lesion formation can be prevented or reversed and enlargement of lesions be slowed or stopped. The earliest lesions are now known to be fatty streaks, largely of cholesterol, which often progress in stages to plaques containing cellular, fibrous and calcified material in addition to the lipids.

The evidence that hyperlipidemia is one of the factors involved in coronary heart disease is very impressive. A most important study carried out in Framingham, Mass. (Gordon and Verter, 1969) in over 5,000 persons for more than 12 hears established a correlation between high concentrations of blood cholesterol and increased risk of heart attack. Although the causes of coronary artery diseases are multiple, one of the most constant factors has been the elevated concentration of lipids in the blood plasma. A combined elevation of cholesterol and triglycerides has been shown (Carlson and Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis et al., 1974).

The reason for most treatment of hyperlipidemia or hyperlipoproteinemia is for arresting, reversing or preventing atherosclerosis. In the past, attempts have been made to lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in U.S. Pat. No. 3,148,114. In addition, several synthetic hypolipidemic agents are now available, namely, clofibrate, D-thyroxine, cholestyramine and nicotinic acid [(Levy and Frederickson, Postgraduate Medicine 47, 130 (1970)]. Clofibrate has the undesirable side-effect of causing hypertrophy of the liver in some patients.

The development of agents capable of reducing elevated blood lipids and of favorably altering blood-lipoprotein patterns is considered by medical authorities to be extremely important for the treatment and prevention of atherosclerosis. Orally active agents are required since patients usually take them for a number of years.

DETAILED DESCRIPTION OF THE INVENTION

The compounds of this invention are new and novel (monosubstituted-amino)heteroaryl carboxylic acids and analogs which have useful biological and pharmacological properties. No hypolipidemic activity has been reported in the literature for these compounds and they are different in structure from other hypolipidemic agents. The compounds of this invention lower serum-lipid concentrations and also minimize atheroma formation in the aorta. These substances also provide the oral administration required of hypolipidemic agents, which patients usually take for many years. The novel compounds of this invention are adequately absorbed from the gastrointestinal tract.

We have now found that the compounds of the present invention can safely and effectively lower both serum sterols and triglycerides in warm-blooded mammals. Such actions on serum-lipid components are considered to be very useful in the treatment of atherosclerosis, especially in contrast to available durgs whose action is much more limited. For some time it has been considered desirable to lower serum-lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically foavorable characteristics possessed by those of the present invention can be safely administered to warm-blooded mammals for the treatment of hyperlipidemic and atherosclerotic states found in patients with or prone to heart attacks, to peripheral or cerebral vascular disease, and to stroke.

The novel compounds of the present invention are, in general, white crystalline solids having characteristic melting points and absorption spectra. They are soluble in organic solvents such as lower alkanol, chloroform, benzene, dimethylformamide, and the like but are generally not very soluble in water. The novel compounds of the present invention, which are organic bases, may be converted to their non-toxic acid-addition or cationic salts with a variety of pharmaceutically acceptable organic and inorganic salt-forming reagents. Thus, acid-addition salts may be formed by admixture of the organic free base in a neutral solvent with one or two equivalents of an acid such as sulfuric, phosphoric, hydrochloric, hydrobromic, trifluoroacetic, citric, ascorbic, and the like. The novel compounds of the present invention in their acidic forms or which contain acidic substituents are converted to their non-toxic organic or inorganic cationic salts for therapeutic use. The sodium or potassium salts which are formed in solution in the course of hydrolysis of their esters can be isolated as the solid alkali metal salts by cooling. Where it is desirable to purify a compound in the form of the acid, the salt is conveniently formed by treating its solution with exactly one equivalent of base and evaporation or lyophilization. Alkaline earth salts are prepared similarly, often using their acetate salts as a conveniently soluble form. Organic base salts such as those of N-methylglucamine are prepared by dissolving equimolar amounts of the acid and the base is hot ethanol or aqueous alcohols and cooling to crystallization.

The (monosubstituted-amino)furan, pyrrole or thiophene carboxylic acids and analogs of this invention are prepared by reaction of loweralkyl aminoheteroaryl carboxylates with suitable alkylating agents such as alkyl, alkenyl, and alkynyl halides, sulfates, tosylates, mesylates or trifluoromethane sulfonates, with or without solvent at 50°-150° C. Suitable solvents are loweralkanols, chloroform, N,N-dimethylformamide, N,N-dimethylacetamide, diglyme, dimethylsulfoxide, acetonitrile, toluene, benzene, hexamethylphosphoramide and like solvents.

The reaction may be carried out with 2 equivalents of these alkyl aminoheteroaryl carboxylates or with one equivalent of base, such as an unreactive organic base such as diisopropylethylamine or an alkali carbonate or bicarbonate, or with a catalytic amount of copper powder when an appropriate halide is used as the alkylating agent. The resulting esters are readily hydrolyzed to the acids in aqueous ethanolic alkali at 25°–100° C. for 1 to 24 hours.

The loweralkyl N-acetyl-(substituted-amino)heteroaryl carboxylates are prepared by reaction of a loweralkyl (acetylamino)heteroaryl carboxylate with an appropriate alkylating agent in the presence of an equivalent of sodium hydride in an inert solvent such as N,N-dimethylformamide, N,N-dimethylacetamide or diglyme at 50°–150° C. These N-acetyl esters are readily hydrolyzed and deacetylated to the acids in boiling aqueous ethanolic dilute alkali or acid.

Alternative methods of preparation are by reductive alkylation of a 4-aminoheteroaryl carboxylate ester which may also be generated in situ by reduction of 4-amino precursors such as a 4-nitro group and the like, or by a borohydride reduction of the chlorimide formed with phosphorus oxychloride from an acylamino ester. For example, an aldehyde plus an aminoheteroaryl carboxylate are reduced under 1–10 atmospheres of hydrogen using a metal catalyst, forming the (monosubstituted-amino)heteroaryl carboxylate ester. Diborane reduction of (alkanoylamino)heteroaryl carboxylate esters such as ethyl 5-hexadecanamido-2-thiophenecarboxylate at room temperature or above for 1–6 hours yields the corresponding (alkylamino)heteroaryl carboxylate esters, in this case ethyl 5-hexadecylamino-2-thiophenecarboxylate. The requisite (alkanoylamino)heteroaryl carboxylate esters are obtained by acylation of the corresponding aminoheteroaryl carboxylate ester with an alkanoyl halide or anhydride. Alternatively, the reduction of the (alkanoylamino)heteroaryl carboxylate is carried out by first forming the corresponding alkylchloroimide with phosphorous oxychloride and base, and then reducing the alkylchloroimide moiety to the alkylamino group with sodium borohydride.

Two types of substitution reactions also yield the compounds of the present invention, namely, reaction of esters or amides of didehydroheteroaryl carboxylic acids with an alkylamine (or its alkali metal salt) and amination of fluoroheteroaryl carboxylate esters. The former type of reaction is carried out by treating a haloheteroaryl compound with the lithium, potassium or sodium salt of an amine (in excess) such as hexadecylamine in diethyl ether or another aprotic solvent. The latter type comprises reacting hexadecylamine or the like with a fluoroheteroaryl carboxylate ester at elevated temperature.

The alkyl halides, acyl halides, and alkyl amines required for the above described alkylation, acylation, and displacement reactions, respectively, may be prepared from the appropriate carboxylic acids or alcohols which are described in the chemical literature, by methods well-known to those skilled in the art.

The novel compounds of the present invention where Z is other than COOH may be readily prepared by treating an acid halide, mixed acid anhydride, or activated ester or amide of a compound of formula I wherein

is COOH with an appropriate hydroxy compound, amine, or salt of a carboxamide or sulfonamide. These reactions are preferably carried out in an inert solvent at a temperature of 5°–125° C. for a period of time of from about 30 minutes to 18 hours or more. In the case of the acid halide and other acid-forming acylating agents, the reaction is carried out in the presence of an acid scavenger such as diisopropylethylamine, 4-dimethylaminopyridine, pyridine, triethylamine, finely powdered sodium carbonate, and the like. The acid halide and anhydride starting materials may be obtained from the corresponding (monosubstituted-amino)heteroaryl carboxylic acids by methods which are well-known in the art or described herein. However, a protecting group on the amino nitrogen is used for best results. The simplest protecting group is provided by protonation of the amine to give an ammonium salt prior to or during formation of the acylating agent. Acylation of this amino group by carefully selected acyl groups such as carbobenzyloxy, carbo-t-butoxy, and trifluoroacetyl provides protection of this group from self-acylation during amide or ester formation. These protecting groups are then removed by catalytic hycrogenation, mild acid treatment and mild alkali treatment, respectively.

Activated esters or amides, which are used to synthesize the esters of the present invention, are carboxymethyl, 4-nitrophenyl, N-oxysuccinimide, 1-imidazolyl and the like. In certain cases, treatment of acids or ordinary esters such as methyl or ethyl with an excess of an appropriate hydroxy-containing substrate in the presence of a Lewis or mineral acid such as boron trifluoride, sulfuric acid, or hydrochloric acid is sufficient to convert the (monosubstituted-amino)heteroaryl carboxylic acids to the appropriate esters.

With certain kinds of substrates for ester formation, it is necessary to form the alkali metal or strong organic base salts of the (monosubstituted-amino)heteroaryl carboxylic acid in order to react them with 2,3-dihydroxypropyl iodide, ethyl chloroacetate and the like. Other esters are prepared from the acids themselves by reaction with diazoalkanes, ethyl diazoacetate or the like.

The (monosubstituted-amino)heteroaryl carboxylic acids and derivatives are prepared by de-acylation of the corresponding N-trifluoroacetyl ester or amide by reacting with an alkali hydroxide such as sodium or potassium hydroxide in a lower alkanol, water or an aqueous lower alkanol at 5° C. to 50° C. Alternatively, certain of these compounds may be prepared by de-acylation of the N-carbo-t-butoxy derivative and the like with mineral acids such as hydrochloric or hydrobromic acid, preferably in glacial acetic acid at 0° C. to 50° C. Also, they are often prepared by removal of the carbobenzyloxy protecting group from the amino nitrogen atom by means of mild catalytic hydrogenation or by treatment with a mineral acid such as hydrobromic acid in glacial acetic acid.

With certain kinds of substrates for amide formation, it is necessary to form the alkali metal or strong organic base salts of these substrates in order to react them with the various aforementioned acylating forms of the (monosubstituted-amino)heteroaryl carboxylic acids. The aminoalkanecarboxylic and aminoalkanesulfonic acids are zwitterionic and must be converted to their cationic salts, suitably in situ. They may also be used in the form of their esters and then hydrolyzed after amide formation. Certain substrates, which are neutral like the carboxamides or slightly acidic like the alkane or arene sulfonamides, are converted to reactive sodium salts by reaction with sodium hydride or other basic reagents.

Alternatively, the free acids may be prepared by hydrolysis of the corresponding nitriles or various amides, imidates or oxazolines. The carboxylic acid moiety may also be generated by oxidation of the corresponding aldehydes, acetophenones, benzyl alcohols, or alkylbenzenes, most often with the use of an amine-protecting group such as trifluoroacetyl or t-butyloxycarbonyl. The carboxaldehyde moiety may be generated by reduction of the corresponding (monosubstituted-amino)heteroaryl carbonitrile with diisobutylaluminum hydride.

Certain derivatives

of the aminoheteroaryl nitrogen atom are useful for providing greater solubility, more uniform and reliable intestinal absorption, and for a certain degree of modification of the pharmacology of the compounds of the present invention. Some of these derivatives can be converted to the corresponding N-H forms by the acidity of the stomach or the alkalinity of the small intestine. Others are converted by metabolic processes. The methyl and carboxymethyl derivatives and the like are prepared by the alkylation, reductive alkylation, and acylamino reduction methods above. Derivatives such as the acetyl and succinyl compounds may be prepared using acetyl chloride, acetic anhydride, succinic anhydride, etc. in the presence of pyridine, triethylamine or the like at temperatures moderate enough to avoid acylation of the amide moiety. The 1-(sodium sulfo)alkyl derivatives are obtained by reaction of the (monosubstituted-amino)heteroaryl carboxylic acid, ester or amide with sodium bisulfite and an aliphatic aldehyde, a polyhydroxyaldehyde such as glyceraldehyde or glucose, or cinnamaldehyde in a mixed organic-aqueous medium. In the case of cinnamaldehyde, the di-sulfonate salts result from addition of the bisulfite to the carbon-nitrogen double bond of the intermediate as well as to the carbon-carbon double bond of cinnamaldehyde itself.

The novel compounds of the present invention are not only potent hypolipidemic agents but also prevent or diminish the formation or enlargement of arterial plaques in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active compound for a subject of about 70 kg. of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compound may be administered in a convenient manner by the oral route. The compounds of the present invention exert a more powerful hypochlolesteremic and antiatherosclerotic effect than the aforementioned adjuvants and medicaments. It is not known how these novel compounds operate in the blood serum and no theory of why these compounds so operate is advanced. It is not intended that the present invention should be limited to any particular mechanism of action of lowering serum lipids or of amelioating atherosclerosis, or be limited to compounds acting by only one mechanism.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active ingredient is such therapeutically useful compositions is such that a suitable dosage will be obtained. Preferred compositions or preparations according to the present invention are prepared so that an oral dosage-unit form contains between about 50 to 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage-unit form is a capsule, it may contain in addition to materials of the above type, a liquid carrier. Various other materials may be present as coatings or to otherwise modify the physical form of the dosage-unit. For instance, tablets, pills, or capsules may be coated with shellac, sugar or both. A syrup or elixir may contain the active compounds, sucrose as a sweetening agent, methyl and propylparabens as preservatives, a dye and flavoring such as cherry or orange flavor. Of course, any material used in preparing any dosage-unit form should be pharmaceutically pure and substantially non-toxic in the amounts employed. In addition, the active ingredients may be incorporated into sustained-release preparations and formulations.

The invention will be described in greater detail in conjunction with the following specific examples.

EXAMPLE 1

Preparation of 4-amino-2-cyanothiophene

A mixture of 15.4 g. of 2-cyano-4-nitrothiophene in 160 ml. of concentrated hydrochloric acid is cooled to 5° C. in an ice bath. To this mixture is added 12 g. of tin metal and the temperature rises to 12°. When the temperature drops to 5° an additional 11.6 g. of tin metal is added. Stirring is continued until all the tin dissolves. At this time the reaction mixture is filtered and the solid washed with ether. The hydrochloride is obtained by recrystallization from methanol.

To 100 ml. of water is added 11.5 g. of 4-amino-2-cyanothiophene hydrochloride and this mixture is cooled in an ice bath. To the mixture is added 7.2 ml. of 10 N sodium hydroxide dropwise. Upon stirring and continued cooling, crystalline product is obtained. The product is filtered and recrystallized from methylene chloride-hexane.

EXAMPLE 2

Preparation of 4-hexadecylamino-2-cyanothiophene

To 13.6 g. of 4-amino-2-cyanothiophene and 13.8 g. of potassium carbonate is added 50 ml. of hexamethylphosphoramide previously dried over molecular sieves. To this mixture is added 31.4 g. of 1-bromohexadecane and the reaction heated to 130°. The temperature is maintained at 130° for 20 hours. After cooling, the reaction is poured into water and the solid filtered. The solid is dissolved in methylene chloride and this solution is then dried over sodium sulfate, filtered through Magnesol and treated with Darco. The filtrate is evaporated and the residue recrystallized from isopropanol to yield the product.

EXAMPLE 3

Preparation of 4-hexadecylamino-2-formylthiophene

Di-isobutylaluminum hydride (14 ml., 25% solution in toluene) is added with stirring to a solution of 2.9 g. of 4-hexadecylamino-2-cyanothiophene in toluene under a nitrogen atmosphere. The temperature rises during the addition and the reaction is then stirred for 1 hour. A solution of methanol in toluene (14 ml., 1:1) is added over 30 minutes and the mixture is poured into vigorously stirred ice-cold aqueous sulfuric acid (125 ml., 5%). After 10 minutes diatomaceous earth (7.5 g.) is added, the mixture filtered and the organic layer separated. The aqueous solution is extracted twice with toluene (25 ml.) and the combined organic layers are washed with aqueous sodium bicarbonate, dried over magnesium sulfate, decolorized with charcoal, filtered and evaporated in vacuo to give crude product. The product is obtained by recrystallization from dichloromethane-hexane.

EXAMPLE 4

Preparation of 2-carbamyl-4-hexadecylaminothiophene

A mixture of 6.9 g. of 4-hexadecylamino-2-cyanothiophene, 80 ml. of methyl cellosolve, and 80 ml. of 1 N sodium hydroxide is refluxed for 21 hours. After cooling in an ice bath, the solid is filtered and thoroughly washed with methylene chloride. The solid is then added to 100 ml. of water and 5 ml. of concentrated hydrochloric acid and stirred for 8 hours. The solid is filtered and recrystallized from isopropanol.

EXAMPLE 5

Preparation of 4-hexadecylamino-2-thiophenecarboxylic acid

A mixture of 4.4 g. of 2-carbamyl-4-hexadecylaminothiophene, 50 ml. of methyl cellosolve, and 50 ml. of 6 N hydrochloric acid is refluxed for 40 hours and then allowed to cool. The solid is filtered and recrystallized from methanol. The solid is then dissolved in hot sodium bicarbonate solution, filtered, and the filtrate is acidified with concentrated hydrochloric acid. The resulting precipitate is collected and recrystallized from isopropanol to yield the product.

EXAMPLE 6

Preparation of ethyl 5-nitro-2-thiophenecarboxylate

To 160 ml. of acetic anhydride cooled to −5° in an ice-salt bath is added 34 ml. of 90% nitric acid dropwise so that the temperature does not rise above 0°. To this mixture is added 62.7 g. of ethyl 2-thiophenecarboxylate dropwise so that the temperature remains below −5°. Reaction is stirred for 1 hour and poured onto ice. The product is filtered, dried, and recrystallized from hexane.

EXAMPLE 7

Preparation of ethyl 5-amino-2-thiophenecarboxylate

A mixture of 60.4 g. of ethyl-5-nitro-2-thiophenecarboxylate and 480 ml. of concentrated hydrochloric acid is cooled in an ice-bath to below −5°. To this mixture is added 72 g. of granular tin in small amounts, keeping the temperature near −5°. After stirring for 6 hours, 575 ml. of 10 N sodium hydroxide is added to neutralize the mixture. Methylene chloride and Celite are added and the mixture is filtered. The methylene chloride layer of the filtrate is separated, dried over sodium sulfate, and filtered through Magnesol. Evaporation affords an oil which is distilled to yield the product.

EXAMPLE 8

Preparation of ethyl 5-hexadecanamido-2-thiophenecarboxylate

To a solution of 8.6 g. of ethyl 5-amino-2-thiophenecarboxylate and 25 ml. of triethylamine in 100 ml. of methylene chloride is added dropwise 16.5 g. of palmitoyl chloride. The reaction mixture is stirred for 20 hours. Evaporation affords an oil. A methylene chloride solution of the oil is filtered and the filtrate passed through Magnesol. Removal of the solvent by evaporation yields a solid which is recrystallized from hexane. A second recrystallization from carbon tetrachloride affords the product.

EXAMPLE 9

Preparation of ethyl 5-hexadecylamino-2-thiophenecarboxylate

To 1.1 g. of ethyl 5-hexadecanamido-2-thiophenecarboxylate is added 5 ml. 1 M borane in tetrahydrofuran. The reaction mixture is refluxed for 1 hour. After cooling, the reaction mixture is poured into 50 ml. of 1 N hydrochloric acid. The solid is collected and then recrystallized from both carbon tetrachloride and ethanol to yield the product.

EXAMPLE 10

Preparation of 5-hexadecylamino-2-thiophenecarboxylic acid

A mixture of 0.1 g. of ethyl 5-hexadecylamino-2-thiophenecarboxylate, 10 ml. of absolute ethanol and 10 ml. of 0.5 N sodium hydroxide is refluxed for 3 hours. The reaction mixture is cooled and then concentrated. The pH of the solution is adjusted to 5.3 and the resulting solid filtered and dried to yield the product.

EXAMPLE 11

Preparation of ethyl 5-nitro-2-furancarboxylate

To a solution of 39 g. of 5-nitro-2-furancarboxylic acid in 200 ml. of ethanol is added 2 ml. of p-toluenesulfonic acid. The reaction is heated for 48 hours. The reaction mixture is evaporated and methylene chloride is added to the residue. The solution is extracted with 10% sodium bicarbonate and dried over anhydrous sodium sulfate. The solution is concentrated and then filtered through Magnesol. The product is obtained by recrystallization from methylene chloride and hexane.

EXAMPLE 12

Preparation of ethyl 5-amino-2-furancarboxylate

A mixture of 53.3 g. of ethyl 5-nitro-2-furancarboxylate, 5 g. of 10% palladium on carbon, and 250 ml. of absolute ethanol is shaken in an atmosphere of hydrogen until no more hydrogen is taken up. The catalyst is filtered and the filtrate evaporated. The thick oily residue is dissolved in a small amount of methylene chloride and the solution is filtered through Magnesol. The solvent is evaporated to yield the product.

EXAMPLE 13

Preparation of ethyl 5-hexadecanamido-2-furancarboxylate

To a solution of 28.7 g. of ethyl 5-amino-2-furancarboxylate, 50 ml. of triethylamine and 300 ml. of methylene chloride is added 51.7 g. of palmitoyl chloride dropwise. The reaction mixture is allowed to stir for 48 hours. The solvent is evaporated and the residue dissolved in a small amount of methylene chloride. The methylene chloride solution is filtered through Magnesol and concentrated to an oil. The product is obtained by cryytallization of the residual oil from hexane.

EXAMPLE 14

Preparation of ethyl 5-hexadecylamino-2-furancarboxylate

A mixture of 1.1 g. of ethyl 5-hexadecanamido-2-furancarboxylate and 5 ml. of 1 M borane in tetrahydrofuran is refluxed on the steam bath for 3 hours. After cooling, the reaction is poured into dilute hydrochloric acid and the resulting solid filtered. The solid is dissolved in methylene chloride and the solution is filtered through Magnesol. The solvent is evaporated to yield the product.

EXAMPLE 15

Preparation of 5-hexadecylamino-2-furancarboxylic acid

A mixture of 2.0 g. of ethyl 5-hexadecylamino-2-furancarboxylate, 10 ml. of ethanol, and 2.0 ml. of 1 N sodium hydroxide is stirred under reflux for 3 hours and then allowed to cool. The mixture is concentrated in vacuo, diluted with water, and adjusted to pH 5 with the dropwise addition of dilute hydrochloric acid. The solid is collected by filtration, washed with water, and dried to yield the product.

EXAMPLE 16

Preparation of ethyl 1-methyl-4-nitro-2-pyrrolecarboxylate

A solution of 2.5 g. of sodium methoxide in 25 ml. of methanol is cooled to 10° C. and a mixture of 7.0 g. of ethyl 4-nitro-2-pyrrolecarboxylate in 15 ml. of methanol is added. After 10 minutes, 18.6 g. of methyl iodide is added. The dark-colored solution is warmed to 35° C. for 0.5 hours, then cooled and allowed to stir at room temperature for 16 hours. Chilling and filtration affords a solid which is collected by filtration and recrystallized from ethanol to yield the product.

EXAMPLE 17

Preparation of ethyl 4-hexadecanamido-1-methyl-2-pyrrolecarboxylate

A solution of 1.5 g. of ethyl 1-methyl-4-nitro-2-pyrrolecarboxylate in 17 ml. of dry tetrahydrofuran is purged for 15 minutes with nitrogen. A catalytic quantity of 5% palladium on carbon is added and a slow stream of hydrogen gas is bubbled in. When the completion of the reaction is indicated by thin layer chromatography, the system is again purged with nitrogen and solution is filtered through Celite. This filtrate is then added to a milky solution of 2.05 g. of palmitoyl chloride, 1 ml. of triethylamine and 10 ml. of dry tetrahydrofuran. The reaction is allowed to stir at 25° C. for 24 hours, diluted with water, and extracted with ether. The extract is dried over magnesium sulfate and evaporated to yield the product as a white solid.

EXAMPLE 18

Preparation of ethyl 4-hexadecylamino-1-methyl-2-pyrrolecarboxylate

A solution of 1.0 g. of ethyl 4-hexadecanamido-1-methyl-2-pyrrolecarboxylate in 10 ml. of dry tetrahydrofuran is added dropwise to a solution of 6 ml. of 1 M borane in tetrahydrofuran under nitrogen and the pale yellow solution is heated to reflux overnight. After cooling and acidification with 1 N aqueous hydrochloric acid followed by neutralization with saturated sodium bicarbonate solution, the solution is extracted with ether. The extract is dried over anhydrous magnesium sulfate and evaporated. The residue is recrystallized from hexane to yield the product as a white solid.

EXAMPLE 19

Preparation of 4-hexadecylamino-1-methyl-2-pyrrolecarboxylic acid

A mixture of 1.0 g. of ethyl 4-hexadecylamino-1-methyl-2-pyrrolecarboxylate and 10 ml. of 40% aqueous sulfuric acid is heated under reflux for 24 hours, allowed to cool and neutralized with sodium acetate. The mixture is extracted with chloroform and the extract is dried over magnesium sulfate and evaporated. The residue is purified by chromatography on a silica gel column by elution with chloroform-acetic acid mixtures. Evaporation of the eluate affords the product.

EXAMPLE 20

Preparation of 5-hexadecylamino-1-methyl-2-pyrrolecarboxylic acid

In a series of chemical reaction analogous to those described in Examples 17–19, methyl 1-methyl-5-nitro-2-pyrrolecarboxylate is converted to 5-hexadecylamino-1-methyl-2-pyrrolecarboxylic acid.

EXAMPLE 21

Preparation of 2-hexadecylamino-5-pyrimidinecarboxylic acid hydrochloride

A mixture of 2.0 g of ethyl 2-methylthio-5-pyrimidinecarboxylate, 3.0 g. of hexadecylamine, and 20 ml. of hexamethylphosphoramide is heated at 110° C. for 10 hours, allowed to cool, and diluted with water. Filtration affords a solid which is crystallized from hexane to yield ethyl 2-hexadecylamino-5-pyrimidinecarboxylate as a tan solid.

The solid is added to a solution of 1.2 g. of potassium hydroxide in 50 ml. of 95% ethanol and the mixture is stirred under reflux for 3 hours, diluted with 50 ml. of water, treated with 1.0 ml. of concentrated hydrochloric acid. The warm mixture is then allowed to cool and the resulting precipitate is collected by filtration and dried to yield the product as a white solid.

EXAMPLE 22

Preparation of 6-hexadecylamino-3-pyridinecarboxylic acid hydrochloride

A mixture of 5.13 g. of methyl 6-chloronicotinate, 7.23 g. of hexadecylamine and 150 ml. of hexamethylphosphoramide is stirred at 130° for 6 hours. Cooling and dilution with water affords a precipitate which is collected by filtration and recrystallized from ethyl acetate and then from acetone to yield methyl 6-hexadecylamino-3-pyridinecarboxylate as a tan solid.

A mixture of the solid, 1.9 g. of potassium hydroxide, 5.0 ml. of water and 50 ml. of methanol is stirred under reflux for 3 hours, allowed to cool and filtered. The solid is warmed with 55 ml. of 10% hydrochloric acid for 2 hours. The mixture is chilled and filtered and the solid is recrystallized from acetone to yield the product as a white solid.

TABLE I

The heteroaryl carboxylic acids shown are prepared from the appropriate aminoheteroaryl compounds and alkyl halides, acyl halides, or alkyl amines using the methods of Examples 1-22 as listed in the table.

| Example No. | Methods of Examples | Compound |
| --- | --- | --- |
| 23 | 1-5 | 4-Hexylamino-2-thiophenecarboxylic acid |
| 24 | 1-5 | 4-Octylamino-2-thiophenecarboxylic acid |
| 25 | 1-5 | 4-Decylamino-2-thiophenecarboxylic acid |
| 26 | 1-5 | 4-Undecylamino-2-thiophenecarboxylic acid |
| 27 | 1-5 | 4-Tetradecylamino-2-thiophenecarboxylic acid |
| 28 | 1-5 | 4-Octadecylamino-2-thiophenecarboxylic acid |
| 29 | 1-5 | 4-(1-Methylpentadecylamino)-2-thiophenecarboxylic acid |
| 30 | 1-5 | 4-(15-Methylhexadecylamino)-2-thiophenecarboxylic acid |
| 31 | 1-5 | 4-(13,13-Dimethyltetradecylamino)-2-thiophenecarboxylic acid |
| 32 | 1-5 | 4-(15,15-Dimethylhexadecylamino)-2-thiophenecarboxylic acid |
| 33 | 1-5 | 4-(10-Undecenylamino)-2-thiophenecarboxylic acid |
| 34 | 1-5 | 4-(3,7-Dimethyl-6-octenylamino)-2-thiophenecarboxylic acid |
| 35 | 1-5 | 4-(2,6,10-Trimethyl-11-dodecenylamino)-2-thiophenecarboxylic acid |
| 36 | 1-5 | 4-(1-Methyl-6-heptenylamino)-2-thiophenecarboxylic acid |
| 37 | 1-5 | 4-(1,1-Diisopropyl-2-propenylamino)-2-thiophenecarboxylic acid |
| 38 | 1-5 | 4-(1,3-Dimethyl-1-ethyl-2-pentenylamino)-2-thiophenecarboxylic acid |
| 39 | 1-5 | 4-(11-Hexadecynylamino)-2-thiophenecarboxylic acid |
| 40 | 1-5 | 4-(6-Methyl-2-heptynylamino)-2-thiophenecarboxylic acid |
| 41 | 1-5 | 4-(1-Isopropyl-1-methyl-2-heptynylamino)-2-thiophenecarboxylic acid |
| 42 | 1-5 | 4-[3-(1,3-Dimethylcyclohexyl)-2-propylamino]-2-thiophenecarboxylic acid |
| 43 | 1-5 | 4-(13-Cyclopentyltridecylamino)-2-thiophenecarboxylic acid |
| 44 | 1-5 | 4-(11-Cyclohexylundecylamino)-2-thiophenecarboxylic acid |
| 45 | 1-5 | 4-(4-Cyclohexyl-2-butenylamino)-2-thiophenecarboxylic acid |
| 46 | 1-5 | 4-(11-Phenylundecylamino)-2-thiophenecarboxylic acid |
| 47 | 1-5 | 4-(4-Chlorobenzylamino)-2-thiophenecarboxylic acid |
| 48 | 1-5 | 4-[3-(4-Fluorophenyl)propylamino]-2-thiophenecarboxylic acid |
| 49 | 1-5 | 4-(4-Decyloxybenzylamino)-2-thiophenecarboxylic acid |
| 50 | 1-5 | 4-(4-Methylbenzylamino)-2-thiophenecarboxylic acid |
| 51 | 1-5 | 4-[3-(3-Trifluoromethyl)propylamino]-2-thiophenecarboxylic acid |
| 52 | 1-5 | 4-Cinnamylamino-2-thiophenecarboxylic acid |
| 53 | 1-5 | 4-[3-(2,4-Dichlorophenyl)propylamino]-2-thiophenecarboxylic acid |
| 54 | 1-5 | 4-[3-(4-Benzyloxyphenyl)propylamino]-2-thiophenecarboxylic acid |
| 55 | 1-5 | 4-[2-(1-Naphthyl)ethylamino]-2-thiophenecarboxylic acid |
| 56 | 6-10 | 5-Heptylamino-2-thiophenecarboxylic acid |
| 57 | 6-10 | 5-Nonylamino-2-thiophenecarboxylic acid |
| 58 | 6-10 | 5-Undecylamino-2-thiophenecarboxylic acid |
| 59 | 6-10 | 5-Dodecylamino-2-thiophenecarboxylic acid |
| 60 | 6-10 | 5-Tridecylamino-2-thiophenecarboxylic acid |
| 61 | 6-10 | 5-Tetradecylamino-2-thiophenecarboxylic acid |
| 62 | 6-10 | 5-Pentadecylamino-2-thiophenecarboxylic acid |
| 63 | 6-10 | 5-Octadecylamino-2-thiophenecarboxylic acid |
| 64 | 6-10 | 5-(3-Methylheptadecylamino)-2-thiophenecarboxylic acid |
| 65 | 6-10 | 5-(15-Methylhexadecylamino)-2-thiophenecarboxylic acid |
| 66 | 6-10 | 5-(14-Methylpentadecylamino)-2-thiophenecarboxylic acid |
| 67 | 6-10 | 5-(2,2,3-Trimethylnonylamino)-2-thiophenecarboxylic acid |
| 68 | 6-10 | 5-(2-Methyloctylamino)-2-thiophenecarboxylic acid |
| 69 | 6-10 | 5-(3,7-Dimethyl-7-octenylamino)-2-thiophenecarboxylic acid |
| 70 | 6-10 | 5-(2-Tetradecenylamino)-2-thiophenecarboxylic acid |
| 71 | 6-10 | 5-(6-Hexadecynylamino)-2-thiophenecarboxylic acid |
| 72 | 6-10 | 5-(15-Hexadecenylamino)-2-thiophenecarboxylic acid |
| 73 | 6-10 | 5-(11-Phenylundecylamino)-2-thiophenecarboxylic acid |
| 74 | 6-10 | 5-[3-Isopropyl-3-(4-tert-butylphenyl)propylamino]-2-thiophenecarboxylic acid |
| 75 | 6-10 | 5-[3-Ethyl-3-(4-tert-butylphenyl)propylamino]-2-thiophenecarboxylic acid |
| 76 | 6-10 | 5-(11-Cyclopropylundecylamino)-2-thiophenecarboxylic acid |
| 77 | 6-10 | 5-(8-Cyclopropyl-2-hexyloctylamino)-2-thiophenecarboxylic acid |
| 78 | 11-15 | 5-Octylamino-2-furancarboxylic acid |
| 79 | 11-15 | 5-Nonylamino-2-furancarboxylic acid |
| 80 | 11-15 | 5-Decylamino-2-furancarboxylic acid |

TABLE I-continued

The heteroaryl carboxylic acids shown are prepared from the appropriate aminoheteroaryl compounds and alkyl halides, acyl halides, or alkyl amines using the methods of Examples 1-22 as listed in the table.

| Example No. | Methods of Examples | Compound |
|---|---|---|
| 81 | 11-15 | 5-Undecylamino-2-furancarboxylic acid |
| 82 | 11-15 | 5-Tridecylamino-2-furancarboxylic acid |
| 83 | 11-15 | 5-Tetradecylamino-2-furancarboxylic acid |
| 84 | 11-15 | 5-Pentadecylamino-2-furancarboxylic acid |
| 85 | 11-15 | 5-Heptadecylamino-2-furancarboxylic acid |
| 86 | 11-15 | 5-Nonadecylamino-2-furancarboxylic acid |
| 87 | 11-15 | 5-(2-Methyloctylamino)-2-furancarboxylic acid |
| 88 | 11-15 | 5-(2,2,3-Trimethylnonylamino)-2-furancarboxylic acid |
| 89 | 11-15 | 5-(14-Methylpentadecylamino)-2-furancarboxylic acid |
| 90 | 11-15 | 5-(15-Methylhexadecylamino)-2-furancarboxylic acid |
| 91 | 11-15 | 5-(3-Methylheptadecylamino)-2-furancarboxylic acid |
| 92 | 11-15 | 5-(3,7-Dimethyl-7-octenylamino)-2-furancarboxylic acid |
| 93 | 11-15 | 5-(2-Tetradecenylamino)-2-furancarboxylic acid |
| 94 | 11-15 | 5-(6-Hexadecynylamino)-2-furancarboxylic acid |
| 95 | 11-15 | 5-(15-Hexadecenylamino)-2-furancarboxylic acid |
| 96 | 11-15 | 5-(11-Phenylundecylamino)-2-furancarboxylic acid |
| 97 | 11-15 | 5-[3-Isopropyl-3-(4-tert-butylphenyl)propylamino]-2-furancarboxylic acid |
| 98 | 11-15 | 5-[3-Ethyl-3-(4-tert-butylphenyl)propylamino]-2-furancarboxylic acid |
| 99 | 11-15 | 5-(11-Cyclopropylundecylamino)-2-furancarboxylic acid |
| 100 | 11-15 | 5-(8-Cyclopropyl-2-hexyloctylamino)-2-furancarboxylic acid |
| 101 | 16-19 | 4-Hexylamino-1-methyl-2-pyrrolecarboxylic acid |
| 102 | 16-19 | 4-Decylamino-1-methyl-2-pyrrolecarboxylic acid |
| 103 | 16-19 | 4-Undecylamino-1-methyl-2-pyrrolecarboxylic acid |
| 104 | 16-19 | 4-Tetradecylamino-1-methyl-2-pyrrolecarboxylic acid |
| 105 | 16-19 | 4-Pentadecylamino-1-methyl-2-pyrrolecarboxylic acid |
| 106 | 16-19 | 4-Octadecylamino-1-methyl-2-pyrrolecarboxylic acid |
| 107 | 16-19 | 4-(3-Methylheptadecylamino)-1-methyl-2-pyrrolecarboxylic acid |
| 108 | 16-19 | 4-(14-Methylpentadecylamino)-1-methyl-2-pyrrolecarboxylic acid |
| 109 | 16-19 | 4-(13,13-Dimethyltetradecylamino)-1-methyl-2-pyrrolecarboxylic acid |
| 110 | 16-19 | 4-(10-Undecenylamino)-1-methyl-2-pyrrolecarboxylic acid |
| 111 | 16-19 | 4-(1,1-Diisopropyl-2-propenylamino)-1-methyl-2-pyrrolecarboxylic acid |
| 112 | 16-19 | 4-(11-Hexadecynylamino)-1-methyl-2-pyrrolecarboxylic acid |
| 113 | 16-19 | 4-[3-(1,3-Dimethylcyclohexyl)-2-propylamino]-1-methyl-2-pyrrolecarboxylic acid |
| 114 | 16-19 | 4-(13-Cyclopentyltridecylamino)-1-methyl-2-pyrrolecarboxylic acid |
| 115 | 16-19 | 4-(11-Phenylundecylamino)-1-methyl-2-pyrrolecarboxylic acid |
| 116 | 16-19 | 4-[3-(4-Benzyloxyphenyl)propylamino]-1-methyl-2-pyrrolecarboxylic acid |
| 117 | 20 | 5-Heptylamino-1-methyl-2-pyrrolecarboxylic acid |
| 118 | 20 | 5-Nonylamino-1-methyl-2-pyrrolecarboxylic acid |
| 119 | 20 | 5-Dodecylamino-1-methyl-2-pyrrolecarboxylic acid |
| 120 | 20 | 2-Tridecylamino-1-methyl-2-pyrrolecarboxylic acid |
| 121 | 20 | 5-Pentadecylamino-1-methyl-2-pyrrolecarboxylic acid |
| 122 | 20 | 5-Octadecylamino-1-methyl-2-pyrrolecarboxylic acid |
| 123 | 20 | 5-(1-Methylpentadecylamino)-1-methyl-2-pyrrolecarboxylic acid |
| 124 | 20 | 5-(13,13-Dimethyltetradecylamino)-1-methyl-2-pyrrolecarboxylic acid |
| 125 | 20 | 5-(10-Undecenylamino)-1-methyl-2-pyrrolecarboxylic acid |
| 126 | 20 | 5-(6-Methyl-6-heptynylamino)-1-methyl-2-pyrrolecarboxylic acid |
| 127 | 20 | 5-(13-Cyclopentyltridecylamino)-1-methyl-2-pyrrolecarboxylic acid |
| 128 | 20 | 5-(11-Phenylundecylamino)-1-methyl-2-pyrrolecarboxylic acid |
| 129 | 20 | 5-(4-Methylbenzylamino)-1-methyl-2-pyrrolecarboxylic acid |
| 130 | 21 | 2-Heptylamino-5-pyrimidinecarboxylic acid |
| 131 | 21 | 2-Octylamino-5-pyrimidinecarboxylic acid |
| 132 | 21 | 2-Decylamino-5-pyrimidinecarboxylic acid |
| 133 | 21 | 2-Tridecylamino-5-pyrimidinecarboxylic acid |
| 134 | 21 | 2-Tetradecylamino-5-pyrimidinecarboxylic acid |
| 135 | 21 | 2-Octadecylamino-5-pyrimidinecarboxylic acid |
| 136 | 21 | 2-(1-Methylpentadecylamino)-5-pyrimidinecarboxylic acid |
| 137 | 21 | 2-(15-Methylhexadecylamino)-5-pyrimidinecarboxylic acid |
| 138 | 21 | 2-(13,13-Dimethyltetradecylamino)-5-pyrimidinecarboxylic acid |
| 139 | 21 | 2-(10-Undecenylamino)-5-pyrimidinecarboxylic acid |
| 140 | 21 | 2-(3,5-Dimethyl-6-octenylamino)-5-pyrimidinecarboxylic acid |
| 141 | 21 | 2-(6-Methyl-6-heptynylamino)-5-pyrimidinecarboxylic acid |
| 142 | 21 | 2-(13-Cyclopentyltridecylamino)-5-pyrimidinecarboxylic acid |
| 143 | 21 | 2-(11-Phenylundecylamino)-5-pyrimidinecarboxylic acid |
| 144 | 21 | 2-(4-Methylbenzylamino)-5-pyrimidinecarboxylic acid |
| 145 | 22 | 6-Hexylamino-3-pyridinecarboxylic acid |
| 146 | 22 | 6-Nonylamino-3-pyridinecarboxylic acid |
| 147 | 22 | 6-Undecylamino-3-pyridinecarboxylic acid |
| 148 | 22 | 6Tetradecylamino-3-pyridinecarboxylic acid |
| 149 | 22 | 6-Pentadecylamino-3-pyridinecarboxylic acid |
| 150 | 22 | 6-(3-Methylheptadecylamino)-3-pyridinecarboxylic acid |
| 151 | 22 | 6-(15-Methylhexadecylamino)-3-pyridinecarboxylic acid |
| 152 | 22 | 6-(14-Methylpentadecylamino)-3-pyridinecarboxylic acid |
| 153 | 22 | 6-(2,2,3-Trimethylnonylamino)-3-pyridinecarboxylic acid |
| 154 | 22 | 6-(1,1-Diisopropyl)-2-propenylamino)-3-pyridinecarboxylic acid |
| 155 | 22 | 6-(11-Hexadecynylamino)-3-pyridine- |

TABLE I-continued

The heteroaryl carboxylic acids shown are prepared from the appropriate aminoheteroaryl compounds and alkyl halides, acyl halides, or alkyl amines using the methods of Examples 1–22 as listed in the table.

| Example No. | Methods of Examples | Compound |
|---|---|---|
| | | carboxylic acid |
| 156 | 22 | 6-[3-(1,3-Dimethylcyclohexyl)-2-propylamino]-3-pyridinecarboxylic acid |
| 157 | 22 | 6-(11-Phenylundecylamino)-3-pyridinecarboxylic acid |
| 158 | 22 | 6-[3-(4-Fluorophenyl)propylamino]-3-pyridinecarboxylic acid |
| 159 | 22 | 6-[3-(4-Benzyloxyphenyl)propylamino]-3-pyridinecarboxylic acid |

EXAMPLE 160

Preparation of 4-hexadecylamino-2-thiophenecarbonyl chloride hydrochloride

A cold solution of 25 g. of 4-hexadecylamino-2-thiophenecarboxylic acid in 500 ml. of 1,2-dimethoxyethane-methylene chloride (4:1) is prepared and dry hydrochloric acid is bubbled through the solution until no more precipitate forms. The solution is treated with 25 ml. thionyl chloride and refluxed until all of the precipitate has dissolved. The solvents are evaporated to yield the product as an orange semi-crystalline mass.

EXAMPLE 161

Preparation of 4-[N-(trifluoroacetyl)-N-(hexadecyl)amino]-2-thiophenecarbonyl chloride A stirred, ice-cold suspension of 9 g. 4-(hexadecylamino)-2-thiophenecarboxylic acid in 100 ml. of dimethoxyethane and 16 ml. of pyridine is treated with 18 ml. trifluoroacetic anhydride at 0° C. The solution is stirred for 30 minutes at room temperature and then diluted with 300 ml. ether and 100 g. ice. After stirring vigorously for 15 minutes, the phases are separated, the ether solution is washed with brine, dried and evaporated to a white, amorphous solid.

To a solution of 9.2 g. of the above solid in 30 ml. methylene chloride and 0.5 ml dimethylformamide is added 5.7 ml. thionyl chloride. After 20 hours at reflux, the solvents are evaporated to yield 4-[N-(trifluoroacetyl)-N-(hexadecyl)amino]-2-thiophenecarbonyl chloride as a light yellow, mobile oil.

EXAMPLE 162

Preparation of 4-[N-(carbobenzyloxy)-N-(hexadecyl)amino]-2-thiophenecarbonyl chloride To 15 g. 4-(hexadecylamino)-2-thiophenecarboxylic acid in 200 ml. warm chloroform is added a solution of 15 g. of sodium carbonate in 150 ml. water. To the vigorously stirred solution is added 10 g. carbobenzyloxy chloride. After 2 hours stirring at 40° C., the organic layer is separated, washed three times with 1 N hydrochloric acid, dried, and evaporated to yield an oil. The oil is dissolved in 300 ml. toluene, treated with 15 ml. thionyl chloride and the solution is refluxed for 5 hours. The solvents are evaporated and the residue is dissolved three times in toluene, evaporating each time, ultimately to yield 4-[N-(carbobenzyloxy)-N-(hexadecyl)amino]-2-thiophenecarbonyl chloride as a viscous, orange oil.

EXAMPLE 163

Preparation of 1-{4-[N-(tert-butyloxycarbonyl)-N-(hexadecyl)amino]-2-thiophenylcarbonyl}imidazole A solution of 10 g. of 4-hexadecylamino-2-thiophenecarboxylic acid in 100 ml. dioxane is treated with 4.0 g. tert-butylazidoformate and 10 ml. pyridine. After stirring at room temperature for 18 hours, the protected amido-acid is precipitated from solution by the addition of 150 ml. water. The solid is collected, thoroughly dried, and dissolved in 200 ml. of a mixture consisting of methylene chloride/dimethoxyethane/pyridine (1:4:1). To this solution is added 5.4 g. 1,1'-carbonyldiimidazole. The solution is stirred overnight at room temperature and the solvents are evaporated to yield 1-{4-[N-(tert-butyloxycarbonyl)-N-(hexadecyl)amino]-2-thiophenecarbonyl)imidazole as an orange oil.

EXAMPLE 164

Preparation of ethyl 4-hexadecylamino-2-thiophenecarboxylate

A solution of 7.20 g. of 4-(hexadecylamino)-2-thiophenecarboxylic acid in 25 ml. of hexamethylphosphoramide is added to a stirred mixture of 0.800 g. of sodium hydride (57% in mineral oil) and 25 ml. of hexamethylphosphoramide. The solution which forms after one hour is treated with 11.0 g. of ethyl iodide and is then stirred at 25° C. for 18 hours. Dilution with water followed by filtration affords a white solid which is crystallized from ethanol to yield ethyl 4-(hexadecylamino)-2-thiophenecarboxylate as a white solid.

EXAMPLE 165

Preparation of methyl 4-hexadecylamino-2-thiophenecarboxylate

A solution of 50.5 g. of 4-(hexadecylamino)-2-thiophenecarboxylic acid and 34.4 ml. of boron trifluoride etherate in 200 ml. of methanol is stirred under reflux for 44 hours, allowed to cool, and poured into 1.20 liters of ice-cold 5% aqueous sodium carbonate solution. The white solid is collected by filtration and recrystallized from benzene-ethanol to yield methyl 4-(hexadecylamino)-2-thiophenecarboxylate as a white solid.

EXAMPLE 166

Preparation of 2,3-dihydroxypropyl 4-hexadecylamino-2-thiophenecarboxylate

A solution of 7.34 g. of 4-(hexadecylamino)-2-thiophenecarboxylic acid, 4.80 g. of 25% aqueous sodium hydroxide, and 12.6 g. of 3-iodo-1,2-propanediol in 50 ml. of hexamethylphosphoramide is stirred for 24 hours at ambient temperature, diluted with 100 ml. of ether and stirred for 5 days at ambient temperature. The mixture is treated with water and extracted with ether. The dried extracts are evaporated to yield 2,3-dihydroxypropyl 4-(hexadecylamino)-2-thiophenecarboxylate as a white solid.

EXAMPLE 167

Preparation of 2-ethoxyethyl 4-hexadecylamino-2-thiophenecarboxylate

A solution of 11.8 g. of 4-(hexadecylamino)-2-thiophenecarboxylic acid, 1.00 g. of 2-ethoxyethanol and 5.35 ml. of boron trifluoride etherate in 200 ml. of toluene is stirred under reflux for 48 hours. The solution is treated with an additional 5.35 ml. of boron trifluoride etherate and refluxing is continued for 120 hours. Dilution with water and methylene chloride followed by filtration affords 2-ethoxyethyl 4-(hexadecylamino)-2-thiophenecarboxylate as a white solid.

EXAMPLE 168

Preparation of 1-(methoxycarbonyl)propyl 4-hexadecylamino-2-thiophenecarboxylate To a solution of 10 g. of 4-hexadecylamino-2-thiophenecarbonyl chloride hydrochloride in 200 ml. methylene chloride is added dropwise a solution of 3 g. methyl α-hydroxybutyrate and 5 g. triethylamine in 100 ml. ether. After 17 hours stirring at room temperature, the precipitate is collected and washed with several protions of ether. The ether solution is washed with water, dried and evaporated to yield 1-(methoxycarbonyl)propyl 4-(hexadecylamino)-2-thiophenecarboxylate as a white solid.

EXAMPLE 169

Preparation of diethyl O-(4-hexadecylamino-2-thiophenecarbonyl)tartrate

A mixture of 4-[N-(trifluoroacetyl)-N-(hexadecyl)amino]-2-thiophenecarbonyl chloride and 1.2 g. of triethylamine in 100 ml. of warm ether is treated with 2.5 g. of diethyl tartarate and refluxed for 24 hours. The hot solution is filtered, the residue is washed with hot ether, and the solution is evaporated. After treatment with aqueous methanolic potassium carbonate, the product is precipitated by acidification, filtered, and dried. Crystallization from acetone yields the product as a white solid.

EXAMPLE 170

Preparation of O-(4-hexadecylamino-2-thiophenecarbonyl)malic acid

A warm solution of 4-[N-(carbobenzyloxy)-N-(hexadecyl)amino]-2-thiophenecarbonyl chloride and 1.3 g. of triethylamine in 100 ml. ether is treated with 2 g. malic acid. An immediate precipitate forms, but the mixture is refluxed for one hour and filtered while hot. The solid is washed several times with hot ether; then the ether is evaporated to yield a white solid. The product is dissolved in tetrahydrofuran (100 ml.) and hydrogenated over 600 mg. 10% palladium-on-carbon at 50 psi until hydrogen uptake stops. The catalyst is filtered, and the solution is evaporated. The residue is crystallized from acetic acid to yield the product as a white solid.

EXAMPLE 171

Preparation of 2-(ethoxycarbonyl)vinyl 4-hexadecylamino-2-thiophenecarboxylate

To a mixture of 4.3 g of 1-{4-[N-(tert-butyloxycarbonyl)-N-(hexadecyl)amino]-2-thiophenecarbonyl}-imidazole and 50 ml. of 5 N sodium hydroxide is added 3 g. ethyl α-formyl acetate. The solution is vigorously stirred for 24 hours. The layers are separated, and the chloroform solution is washed once with 50 ml. 1 N sodium hydroxide. The solvent is evaporated and the residue is heated for 30 minutes at 40° C. in 50 ml. anhydrous trifluoroacetic acid. The solvent is again evaporated and the oil is crystallized from acetone to yield the product as a light yellow solid.

TABLE II

| Example No. | Method of Example | Compound |
|---|---|---|
| 173 | 164 | Ethyl 4-undecylamino-2-thiophenecarboxylate |
| 174 | 165 | Methyl 4-(15-methylpentadecylamino)-2-thiophenecarboxylate |
| 175 | 166 | 2,3-Dihydroxypropyl 4-(10-undecenylamino)-2-thiophenecarboxylate |
| 176 | 167 | 2-Ethoxyethyl 4-(11-hexadecynylamino)-2-thiophenecarboxylate |
| 177 | 168 | 1-(Carbomethoxy)propyl 4-(13-cyclopentyltridecylamino)-2-thiophenecarboxylate |
| 178 | 169 | Diethyl O—{4-[3-(1,3-dimethylcyclohexyl)propylamino]-2-thiophenecarbonyl}tartrate |
| 179 | 170 | O—[4-(11-Phenylundecylamino)-2-thiophenecarbonyl]malic acid |
| 180 | 171 | 2-(Carboethoxy)vinyl 4-(4-methylbenzylamino)-2-thiophenecarboxylate |
| 181 | 164 | Ethyl 4-(8-cyclopropyl-2-hexyloctylamino)-2-thiophenecarboxylate |
| 182 | 164 | Isopropyl 5-(15-hexadecenylamino)-2-thiophenecarboxylate |
| 183 | 165 | Methyl 5-(2,2,3-trimethylnonylamino)-2-thiophenecarboxylate |
| 184 | 166 | 3-Hydroxypropyl 5-pentadecylamino-2-thiophenecarboxylate |
| 185 | 167 | 2-Ethoxyethyl 5-octylamino-2-thiophenecarboxylate |
| 186 | 168 | 1-(Carbomethoxy)ethyl 5-(3-methylheptadecylamino)-2-thiophenecarboxylate |
| 187 | 169 | Diethyl O—(5-hexadecylamino-2-thiophenecarbonyl)tartrate |
| 188 | 170 | O—[5-(6-Hexadecynylamino)-2-thiophenecarbonyl]malic acid |
| 189 | 171 | 2-(Carboethoxy)vinyl 5-(2-methyloctylamino)-2-thiophenecarboxylate |
| 190 | 164 | 3-Hydroxypropyl 5-hexadecylamino-2-furancarboxylate |
| 191 | 164 | Methyl 5-undecylamino-2-furancarboxylate |
| 192 | 166 | 2,3-Dihydroxypropyl 5-(11-phenylundecylamino)-2-furancarboxylate |
| 193 | 166 | 2-Ethoxyethyl 5-[3-isopropyl-3-(4-tert-butylphenyl)propylamino]-2-furancarboxylate |
| 194 | 169 | 1-(Carbomethoxy)propyl 5-(3,7-dimethyl-7-octenylamino)-2-furancarboxylate |
| 195 | 169 | Diethyl O—[5-(14-methylpentadecylamino)-2-furancarbonyl]tartrate |
| 196 | 170 | O—[5-(2-Tetradecenylamino)-2-furancarbonyl]malic acid |
| 197 | 170 | 2-(Carboethoxy)vinyl 5-(15-hexadecenylamino)-2-furancarboxylate |
| 198 | 169 | 2-(Carboethoxy)vinyl 5-octylamino-2-furancarboxylate |
| 199 | 164 | Methyl 4-tetradecyl-1-methyl-2-pyrrolecarboxylate |
| 200 | 165 | Methyl 4-(13,13-dimethyltetradecylamino)-1-methyl-2-pyrrolecarboxylate |
| 201 | 166 | 2,3-Dihydroxypropyl 4-(11-hexadecynylamino)-1-methyl-2-pyrrolecarboxylate |
| 202 | 167 | 2-Ethoxyethyl 4-[3-(1,3-dimethylcyclohexyl-2-propylamino]-1-methyl-2-pyrrolecarboxylate |
| 203 | 168 | Carbomethoxymethyl 4-[3-(4-benzyloxyphenyl)propylamino]-1-methyl-2-pyrrolecarboxylate |
| 204 | 169 | Diethyl O—[4-(13-cyclopentyltridecylamino)-1-methyl-2-pyrrolecarbonyl]-tartrate |
| 205 | 170 | O—[4-(10-Undecenylamino)-1-methyl-2-pyrrolecarbonyl]malic acid |
| 206 | 171 | 2-(Carboethoxy)vinyl 4-(hexadecylamino)-1-methyl-2-pyrrolecarboxylate |
| 207 | 164 | Methyl 5-pentadecyl-1-methyl-2- |

TABLE II-continued

| Example No. | Method of Example | Compound |
|---|---|---|
| | | pyrrolecarboxylate |
| 208 | 165 | Methyl 5-(6-methyl-6-heptynylamino)-1-methyl-2-pyrrolecarboxylate |
| 209 | 166 | 2,3-Dihydroxypropyl 5-hexadecylamino-1-methyl-2-pyrrolecarboxylate |
| 210 | 167 | 2-Ethoxyethyl 5-(10-undecenylamino)-1-methyl-2-pyrrolecarboxylate |
| 211 | 168 | 1-(Carbomethoxy)ethyl 5-(13-cyclopentyltridecylamino)-1-methyl-2-pyrrolecarboxylate |
| 212 | 169 | Diethyl O—[5-(13,13-dimethyltetradecylamino)-1-methyl-2-pyrrolecarbonyl]tartrate |
| 213 | 170 | O—[5-(4-Methylbenzyl)-1-methyl-2-pyrrolecarbonyl]malic acid |
| 214 | 171 | 2-(Carboethoxy)vinyl 5-hexadecylamino-1-methyl-2-pyrrolecarboxylate |
| 215 | 165 | Methyl 2-hexadecylamino-5-pyrimidinecarboxylate |
| 216 | 165 | Methyl 2-tetradecylamino-5-pyrimidinecarboxylate |
| 217 | 165 | 2,3-Dihydroxypropyl 6-pentadecylamino-3-pyridinecarboxylate |
| 218 | 165 | 2,3-Dihydroxypropyl 2-(11-phenylundecylamino)-5-pyrimidinecarboxylate |
| 219 | 167 | 2-Ethoxyethyl 6-(15-methylpentadecylamino)-3-pyridinecarboxylate |
| 220 | 168 | 1-(Carbomethoxy)ethyl 6-(2,2,3-trimethylnonylamino)-3-pyridinecarboxylate |
| 221 | 169 | Diethyl O—{6-[3-(1,3-dimethylcyclohexyl)-2-propylamino]-3-pyridinecarbonyl}tartrate |
| 222 | 170 | O—[2-(6-Methyl-6-heptynylamino)-5-pyrimidinecarbonyl]malic acid |
| 223 | 171 | 2-(Carboethoxy)vinyl 6-[3-(4-fluorophenyl)propylamino]-3-pyridinecarboxylate |
| 224 | 165 | 2,3-Dihydroxypropyl 6-(10-undecenylamino)-3-pyridinecarboxylate |
| 225 | 167 | 2,3-Dihydroxypropyl 2-(4-methylbenzylamino)-5-pyrimidinecarboxylate |

EXAMPLE 226

Preparation of 1-(4-hexadecylamino-2-thiophenecarbonyl)piperidine

To a chilled solution of 35 ml. of piperidine, 2.5 ml. of triethylamine and 0.6 g. of dimethylaminopyridine in 100 ml. of diethyl ether is added (½ hour) a solution of 8.3 g. of 4-hexadecylamino-2-thiophenecarbonyl chloride hydrochloride in 50 ml. of ether. The solution is warmed to room temperature and maintained there for two hours. The solution is heated to reflux for an additional 2 hours at which time the reaction is complete. The solution is cooled, extracted twice with water and dried. The solvent is removed in vacuo and the solid is recrystallized from ether to yield the product as a white solid.

EXAMPLE 227

Ethyl N-(4-hexadecylamino-2-thiophenecarbonyl)glycinate

To a solution of 18 g. of 4-hexadecylamino-2-thiophenecarboxylic acid in dioxane-methylene chloride (1:1) is added gaseous hydrogen chloride for 10 minutes. The slurry is cooled and 18 ml. of thionyl chloride added. The slurry is brought to reflux for 2 hours and then concentrated under vacuum (thrice diluting with dioxane each time). The final amber solution is diluted with 100 ml. of dioxane and this solution added to freshly prepared ethyl glycinate in 300 ml. of methylene chloride containing 1 g. of dimethylaminopyridine and 10 ml. of triethylamine. After 16 hours at room temperature, the reaction is refluxed for 2 hours, cooled and filtered. The mother liquor is extracted with water and 10% hydrochloric acid. The solution is dried and concentrated in vacuo to an amber liquid. A sample is preabsorbed on silica and eluted with ether. Evaporation of the eluate yields a solid which is recrystallized from acetonitrile to yield the product as a white solid.

EXAMPLE 228

Preparation of N-(4-hexadecylamino-2-thiophenecarbonyl)glycine

A mixture of 26 g. of ethyl N-(4-hexadecylamino-2-thiophenecarbonyl)glycinate, 110 ml. of 1 N sodium hydroxide solution; and 100 ml. of ethanol is stirred at ambient temperature for 2 hours and then partially evaporated. The aqueous solution is washed with diethyl ether, acidified with 6 N hydrochloric acid, and filtered. The white solid is dried in vacuo and recrystallized from acetone to yield the product as a white solid.

EXAMPLE 229

Preparation of 4-(hexadecylamino)-N-(phenylsulfonyl)-2-thiophenecarboxamide

A solution of 31.4 g. of benzenesulfonamide in 250 ml. of dry dimethylacetamide is added dropwise, with stirring and cooling, to a suspension of 5.5 g. of sodium hydride in 100 ml. of dry dimethylacetamide during 30 minutes at room temperature. Stirring is continued for 30 minutes. In the meantime, a mixture of 36.2 g. of 4-(hexadecylamino)-2-thiophenecarboxylic acid in 100 ml. of methylene chloride, 300 ml. of dimethoxyethane, and 40 ml. of thionyl chloride is refluxed for 1 hour and 15 minutes. The solution is evaporated and to the resulting oil residue is added, in one portion, the previously prepared mixture of sodium benzenesulfonamide in dimethylacetamide. The mixture is stirred for 30 minutes, without cooling, and then filtered. The filtrate is poured into 2 l. of water and 250 ml. of saturated sodium chloride solution. The product is collected by filtration and then dissolved in methylene chloride, the mixture is filtered through diatomaceous earth, and brine is added to break the emulsion. The layers are separated, the organic phase is dried and evaporated. The residue is crystallized from toluene to yield the product as a white solid.

EXAMPLE 230

Preparation of N-(4-hexadecylamino-2-thiophenecarbonyl)methanesulfonamide

A solution of 25 g. of 4-hexadecylamino-2-thiophenecarbonyl chloride hydrochloride and 5.6 g. of methanesulfonamide in 250 ml. of pyridine is stirred under reflux for 2 hours and then concentrated in vacuo. The residue is partitioned between water and diethyl ether; the aqueous layer acidified with 1 N hydrochloric acid and the organic layer seperated, dried over magnesium sulfate, and evaporated. Crystallization of the residual white solid from 60% aqueous acetic acid and then from methylene chloride-hexane affords the product as a white solid.

EXAMPLE 231

Preparation of N-(4-hexadecylamino-2-thiophenecarbonyl)benzamide

One gram of a 50% oil dispersion of sodium hydride is washed with petroleum ether by decantation, dried, and suspended in 5 ml. of tetrahydrofuran. To this stirred mixture is added a solution of 2.42 g. of benzamide in 5 ml. of tetrahydrofuran in one portion. An initial hydrogen evolution is observed. While stirring (30 minutes), the sodium hydride gradually disappears and a white, milky, turbid mixture forms. A solution of 0.9 g. of 4-[N-(trifluoroacetyl)-4-(hexadecyl)amino]-2-thiophenecarbonyl chloride in 3 ml. of tetrahydrofuran is added dropwise during 5 minutes to the mixture. The whole milky mixture is stirred at room temperature under nitrogen for one hour. The mixture is then poured into water and extracted with ether. The ether extract is washed with water and brine and dried over sodium sulfate. Evaporation of the solvent affords a pale yellow solid. The solid is recrystallized from ether/acetonitrile (50/50) and then from acetonitrile to yield the product as a white solid.

EXAMPLE 232

Preparation of N-(4-hexadecylamino-2-thiophenecarbonyl)pyrrolidine

A warm solution of 1.0 g. of 4-[N-(carbobenzyloxy)-N-hexadecylamino]-2-thiophenecarbonyl chloride and 1.3 g. of triethylamine in 100 ml. of ether is added to 1.2 g. of pyrrolidine. A precipitate forms; the mixture is stirred under reflux for 1 hour, filtered, and extracted with hot ether. The extract is evaporated and a solution of the resulting residue in 100 ml. of tetrahydrofuran is shaken under 50 psi of hydrogen in the presence of 0.6 g. of 10% palladium on carbon. The mixture is filtered and the filtrate evaporated. The residue is crystallized from acetic acid to yield the product as a white solid.

EXAMPLE 233

Preparation of N-(2,3-dihydroxypropyl)-4-hexadecylamino-2-thiophenecarboxamide To a mixture containing 4.1 g. of 1-{4-[N-(tert-butyloxycarbonyl)-N-(hexadecyl)amino]-2-thiophenecarbonyl}imidazole, 50 ml. of chloroform, and 50 ml. of 5 N sodium hydroxide is added 1.1 g. of 3-amino-1,2-propanediol. The solution is vigorously stirred for 24 hours, the layers are separated, and the chloroform solution is washed once with 50 ml. of 1 N sodium hydroxide. The solvent is evaporated and the residue is heated for 30 minutes at 40° C. in 50 ml. of anhydrous trifluoroacetic acid. The solvent is again evaporated and the oil is crystallized from acetone to yield light yellow crystals of N-(2,3-dihydroxypropyl)-4-hexadecylamino-2-thiophenecarboxamide.

TABLE III

The heteroaryl carboxamides shown are prepared from the corresponding carboxylic acids (Table I) by the methods of Examples 227-233 as listed in the table. The requisite carboxylic acid derivatives are prepared by the methods of Examples 160-163.

| Example No. | Method of Example | Compound |
| --- | --- | --- |
| 234 | 226 | 1-[4-(13,13-Dimethyltetradecylamino)-2-thiophenecarbonyl]piperidine |
| 235 | 227 | Ethyl N—[4-(10-undecenylamino)-2-thiophenecarbonyl]glycinate |
| 236 | 228 | N—[4-(10-Undecenylamino)-2-thiophenecarbonyl]glycine |
| 237 | 229 | 4-(11-Cyclohexylundecylamino)-N—(phenylsulfonyl)-2-thiophenecarboxamide |
| 238 | 230 | N—[4-(6-Methyl-2-heptynylamino)-2-thiophenecarbonyl]methanesulfonamide |
| 239 | 231 | N—[4-(11-Phenylundecylamino)-2-thiophenecarbonyl]benzamide |
| 240 | 232 | 1-[4-(4-Methylbenzylamino)-2-thiophenecarbonyl]pyrrolidine |
| 241 | 233 | N—(2,3-Dihydroxypropyl)-4-[N-(2,3-Dihydroxypropyl)-4-[2-(1-naphthyl)ethylamino]-2-thiophenecarboxamide |
| 242 | 226 | 1-[5-(15-Hexadecenylamino)-2-thiophenecarbonyl]pyrrolidine |
| 243 | 227 | Ethyl N—[5-(2,2,3-trimethylnonylamino-2-thiophenecarbonyl]glycinate |
| 244 | 227 | Ethyl N—(5-hexadecylamino-2-thiophenecarbonyl)glycinate |
| 245 | 228 | N—(5-Hexadecylamino-2-thiophenecarbonyl)glycine |
| 246 | 229 | 5-(11-Phenylundecyl)-N—(phenylsulfonyl)-2-thiophenecarboxamide |
| 247 | 230 | N—[5-(15-Hexadecenylamino)-2-thiophenecarbonyl]methanesulfonamide |
| 248 | 231 | N—[5-(8-Cyclopropyl-2-hexyloctylamino)-2-thiophenecarbonyl]benzamide |
| 249 | 232 | 1-{5-[3-Ethyl-3-(4-tert-butylphenyl)-propylamino]-2-thiophenecarbonyl}-pyrrolidine |
| 250 | 233 | 5-[3-Isopropyl-3-(4-tert-butylphenyl)-propylamino]N—(2,3-dihydroxypropyl)-2-thiophenecarboxamide |
| 251 | 231 | 1-(5-Octylamino-2-furancarbonyl)-piperidine |
| 252 | 227 | Ethyl N—(5-hexadecylamino-2-furancarbonyl)glycinate |
| 253 | 232 | N—(5-Hexadecylamino-2-furancarbonyl)-glycine |
| 254 | 231 | 5-(15-Hexadecenyl)N—(phenylsulfonyl)-2-furancarboxamide |
| 255 | 231 | N—[5-(11-Phenylundecylamino)-2-furancarbonyl]benzamide |
| 256 | 232 | 1-[5-(8-Cyclopropyl-2-hexyloctylamino)-2-furancarbonyl]piperidine |
| 257 | 226 | 1-(4-Hexadecylamino-1-methyl-2-pyrrolecarbonyl)piperidine |
| 258 | 227 | Ethyl N—[5-(10-undecenylamino)-1-methyl-2-pyrrolecarbonyl]glycinate |
| 259 | 228 | N—[5-(10-Undecenylamino)-1-methyl-2-pyrrolecarbonyl]glycine |
| 260 | 229 | 4-(14-Methylpentadecylamino)-1-methyl-N—(phenylsulfonyl)-2-pyrrolecarboxamide |
| 261 | 230 | N—(5-Hexadecylamino-1-methyl-2-pyrrolecarbonyl)methanesulfonamide |
| 262 | 231 | N—[5-(11-Phenylundecylamino)-1-methyl-2-pyrrolecarbonyl]benzamide |
| 263 | 232 | 1-(4-Hexylamino-2-methyl-2-pyrrolecarbonyl)pyrrolidine |
| 264 | 233 | 5-(11-Hexadecynylamino)-1-methyl-N—(2,3-dihydroxypropyl)-2-pyrrolecarboxamide |
| 265 | 226 | 1-[2-(15-Methylhexadecylamino)-5-pyrimidinecarbonyl]pyrrolidine |
| 266 | 227 | Ethyl N—(2-hexadecylamino-5-pyrimidinecarbonyl)glycinate |
| 267 | 228 | N—(2-Hexadecylamino-5-pyridinecarbonyl)glycine |
| 268 | 229 | 6-(11-Phenylundecylamino)-N—(phenylsulfonyl)-3-pyridinecarboxamide |

TABLE III-continued

The heteroaryl carboxamides shown are prepared from the corresponding carboxylic acids (Table I) by the methods of Examples 227–233 as listed in the table. The requisite carboxylic acid derivatives are prepared by the methods of Examples 160–163.

| Example No. | Method of Example | Compound |
|---|---|---|
| 269 | 230 | N—(6-Octylamino-3-pyridinecarbonyl-methanesulfonamide |
| 270 | 231 | N—[6-(11-Hexadecynylamino)-3-pyridinecarbonyl)benzamide |
| 271 | 232 | 1-[2-(13-Cyclopentyltridecylamino)-5-pyrimidinecarbonyl]piperidine |
| 272 | 233 | 6-Tetradecyl-N—(2,3-dihydroxylpropyl)-3-pyridinecarboxamide |

TABLE IV

The heteroaryl carboxaldehydes shown are prepared from the appropriate aminoheteroaryl carbonitrile and alkyl halide by the methods of Examples 2 and 3 except for Examples 278, 279, 285 and 286. Using 6-chloronicotinonitrile, the intermediate for Examples 279 and 286 is formed by the procedure of Example 22. Employing 2-chloro-5-cyanopyrimidine, the intermediate for Examples 278 and 285 is prepared by the method of Example 21.

| Example No. | Compound |
|---|---|
| 273 | 4-Hexylamino-2-thiophenecarboxaldehyde |
| 274 | 5-Heptylamino-2-thiophenecarboxaldehyde |
| 275 | 5-Octylamino-2-furancarboxaldehyde |
| 276 | 4-Nonylamino-1-methyl-2-pyrrolecarboxaldehyde |
| 277 | 5-Decylamino-1-methyl-2-pyrrolecarboxaldehyde |
| 278 | 2-Undecylamino-5-pyrimidinecarboxaldehyde |
| 279 | 6-Dodecylamino-3-pyridinecarboxaldehyde |
| 280 | 4-Tridecylamino-2-thiophenecarboxaldehyde |
| 281 | 5-Tetradecylamino-2-thiophenecarboxaldehyde |
| 282 | 4-pentadecyl-1-methyl-2-pyrrolecarboxaldehyde |
| 283 | 5-Hexadecylamino-2-furancarboxaldehyde |
| 284 | 5-Heptadecylamino-1-methyl-2-pyrrolecarboxaldehyde |
| 285 | 2-Octadecylamino-5-pyrimidinecarboxaldehyde |
| 286 | 6-Nonadecylamino-3-pyridinecarboxaldehyde |
| 287 | 4-(1-Methylpentadecylamino)-2-thiophenecarboxaldehyde |
| 288 | 5-(3-Methylheptadecylamino)-2-thiophenecarboxaldehyde |
| 289 | 5-(14-Methylpentadecylamino)-2-furancarboxaldehyde |
| 290 | 4-(13,13-Dimethyltetradecylamino)-1-methyl-2-pyrrolecarboxaldehyde |
| 291 | 5-(10-Undecenylamino)-2-furancarboxaldehyde |
| 292 | 5-(10-Undecenylamino)-2-thiophenecarboxaldehyde |
| 293 | 5-(6-Hexadecynylamino)-1-methyl-2-pyrrolecarboxaldehyde |
| 294 | 4-(3,7-Dimethyl-6-octenylamino)-2-thiophenecarboxaldehyde |
| 295 | 5-(11-Phenylundecylamino)-2-furancarboxaldehyde |

I claim:
1. The compound 5-(10-undecenylamino)-2-thiophenecarboxylic acid.

* * * * *